United States Patent [19]

Prècausta et al.

[11] 4,169,761

[45] Oct. 2, 1979

[54] PROCESS FOR THE CULTIVATION OF VIRUSES

[75] Inventors: Pierre Prècausta, 1700 Big Trail Rd., Walled Lake, Mich. 48088; Marc Bugand, Calvire; Philippe Comte, Ste. Foy-les-Lyon; Georges Zwingelstein, Villeurbanne, all of France

[73] Assignee: Institut Merieux, Lyon, France

[21] Appl. No.: 918,962

[22] Filed: Jun. 23, 1978

[30] Foreign Application Priority Data

Jun. 30, 1977 [FR] France ............................. 77 20115

[51] Int. Cl.² .......................... C12B 3/00; C12K 9/00

[52] U.S. Cl. ................................................. 435/235
[58] Field of Search ............................. 195/1.1, 1.8

[56] References Cited

PUBLICATIONS

Stephenson—Chem. Abst., vol. 84 (1976) p. 40448t.

*Primary Examiner*—Sam Rosen
*Attorney, Agent, or Firm*—Cushman, Darby & Cushman

[57] ABSTRACT

Viruses, especially rabies virus, can be cultivated on an industrial scale using a fermenter containing a suspension of cells and also collagen fibres.

14 Claims, No Drawings

PROCESS FOR THE CULTIVATION OF VIRUSES

This invention relates to a process for cultivating a virus, which is suitable, in particular, for the industrial cultivation of rabies virus so as to obtain viral suspensions which can be used in the manufacture of vaccines.

Usually, the cultivation of rabies virus is carried out in a general manner by cultivating the virus on monocellular layers in flasks. This known technique possesses the disadvantage that it is necessary, especially for quantity production, to use a large number of flasks which involves a considerable number of operations and leads to a high cost price. Likewise for viruses other than rabies virus it is necessary to cultivate them on mono-molecular layers and the same disadvantages are present.

Attempts have already been made to overcome this difficulty by carrying out the culture of the rabies virus on cells placed in a fermenter, that is to say a large vessel containing, in the appropriate liquid nutritive medium, a suspension of the said cells. However, it has been found that the cells behave badly under these conditions and it is not possible to obtain the virus industrially by this method.

The present invention is intended to overcome these disadvantages and to provide a process for the cultivation of a virus which can be carried out on an industrial scale in fermenters, even when using cells which, normally, are not suitable for use in a fermenter. The present invention also aims to reduce the cost price significantly by using such an industrial process.

According to the present invention there is provided a process for the culture of a virus in a fermenter which comprises cultivating the virus in the fermenter containing, in an appropriate nutritive medium, a suspension of the cells and of collagen fibres.

The term "collagen fibres", as used herein, means fibres of collagen possessing a high degree of purity and which are in a form such that the fibres can be dispersed to obtain a suspension. Such fibres can be prepared from the supporting tissues of animals and, in particular, from skins, as described in, for example, French Pat. No. 1,568,829, the disclosure of which is hereby incorporated by reference.

Generally, it is preferred to use collagen fibres extracted from the skins of young cattle, which have been purified and dehydrated, the fibres having been properly sterilised, for example using dry heat.

The amount of fibres in the fermenter is generally from 1 to 20 grams and preferably 2 to 8 grams/liter.

The cultivation is preferably carried out with agitation and at a temperature up to 40° C. Following the culture, it is generally sufficient to stop the agitation so that the fibres separate and deposit on the base of the fermenter.

Preferably, and, in particular, for rabies, it is desirable to carry out a first culture, for example for 2 to 6 days, eliminate the supernatant material and then carry out a second cultivation using a fresh nutritive medium after which the supernatant material is collected.

The supernatant liquid, optionally after having lysed the cells, is then subjected to the customary treatments depending on its intended use, for example as a vaccine.

The cells used for the culture are preferably those cells traditionally used in monolayers in flasks. It is preferred to use cells which have been prepared in the form of a suspension from layers obtained by the introduction of a proteolytic enzyme such as trypsin or pronase or from cellular cultures which have been multiplied in the fermenter, with or without collagen fibres. It is particularly suitable to use cells in the process of the present invention such as NIL 2, lines obtained from the embryos of hamsters, or IFFA 3, PK 15, WI 38 and MRC 5.

Preferably the concentration of the cells in the fermenter is from 50,000 to 500,000 cells/milliliter.

Among the strains of virus which can be cultivated by the process of the present invention there may be mentioned, in particular, rabies virus and especially the rabies strains of the fixed type such as Pasteur CVS or Pitman Moore or modified type such as Flury HEP, Flury LEP, SAD. Other viruses which can be cultivated according to the present invention, optionally after having been subjected to periods of adaptation on the type of cellular material being used as a stationary layer or on collagen fibres kept in suspension.

The liquid nutritive medium may be one of those traditionally used in the cultivation of viruses and no particular requirements are necessary. It can be, for example, a saline solution containing aminoacids, vitamins, glucides, peptones and optionally serum, for example of calves or of chickens, for example Eagle or Stocker MacPherson medium.

The cultivation can be carried out in a traditional manner, preferably at a pH from 6 to 8, aerating and optionally adding a sufficient quantity of carbon dioxide gas.

The following Examples further illustrate the present invention.

EXAMPLE I

A cellular suspension was prepared from layers of NIL 2 cells using trypsin in glass flasks. The resulting cellular suspension was recovered. An amount of material was prepared so that the final concentration in the fermenter to be used was from 150,000 to 300,000 cells/milliliter.

Collagen fibres in an amount so as to provide 2 to 8 grams of fibres/liter of the suspension ready for use were sterilised. This quantity was put in suspension in a nutritive medium. The following materials were introduced, in no special order, into the fermenter in a sterile manner: the nutritive medium, the cell suspension, the suspension of collagen and the seeding viral suspension in amounts so as to obtain the desired volume in relation to the dimensions of the fermenter. This was agitated and the surface aerated with air filtered through a sterilising membrane, the incubation being carried out at a temperature of, say, 37° C.

The multiplication of the cells was controlled by taking a daily count.

After 2 to 6 days agitation was stopped and the collagen fibres allowed to settle on the base of the fermenter. The supernatant liquid was then eliminated.

A fresh nutritive medium was then added in a sterile manner to the fermenter which was then agitated and aerated as before. When the concentration of the viral antigel obtained was sufficient, agitation and aeration were stopped again and recovery of the resulting supernatant liquid was effected under the same conditions as previously.

The suspension was filtered or centrifuged to eliminate cellular debris and some fibrous debris which can be present. The viral suspension thus obtained was then inactivated, for example by using $\beta$-propiolactone for a sufficient time. The preparation can then be either lyophilised or put in a pure liquid form or mixed with an adjuvant or other vaccines.

A convenient anti-rabies vaccine was thus obtained.

EXAMPLE II

A suspension of IFFA 3 cells was obtained using trypsin and the suspension was mixed with sterile collagen and virus of the Pasteur type. The nutritive medium was that of Stocker.

The culture was carried out with agitation (20 to 100 turns per minute) with surface aeration as in the preceding Example. When the desired cellular concentration had been reached the agitation and aeration were stopped and after the fibres had deposited the supernatant liquid was removed.

Fresh nutritive medium free from serum was then introduced in a sterile manner in the fermenter and the agitation and aeration recommenced.

When the concentration of viral antigen was considered to be satisfactory, the agitation and aeration were once again stopped and the viral suspension recovered.

This suspension was filtered on a sterilising membrane and inactivated by, for example, the action of beta-propiolactone. After testing, the preparation could be mixed in predetermined amounts with a sterile alumina gel suspension and then distributed in single or multi-dose bottles.

EXAMPLE III

A suspension of cells of the WI 38 line was obtained using trypsin. Additionally, a predetermined weight of collagen fibres was sterilised. A sufficient volume of seeding virus, modified HEP strain, was prepared.

Each constituent was introduced in a sterile manner into the fermenter and Stocker nutritive medium was added to give the final desired volume. The concentration of fibres was within the range 2 to 8 grams/liter, the concentration of cells being of the order of 100,000 to 200,000 cells per milliliter.

The vessel was agitated 20 to 100 turns per minute and the surface was aerated with the aid of air filtered through a sterilising membrane.

When the multiplication of the cells was sufficient, agitation and aeration were stopped, the collagen fibres were allowed to settle and the supernatant liquid was removed. A fresh nutritive medium free from serum was then added in a sterile manner to the fermenter and the agitation and aeration recommenced. When the multiplication of the viral antigen was considered to be satisfactory, agitation and aeration were stopped and the viral suspension recovered after decantation from the fibres.

The suspension was filtered through a sterilising membrane and then placed into 10 liter, for example, vessels. After testing, the preparation could be mixed with a lactose-based substrate and distributed into single dose bottles which could then be lyophilised.

We claim:

1. Process for the cultivation of a virus which comprises cultivating the virus in a fermenter containing, in an appropriate nutritive medium, a suspension of cells and collagen fibres.

2. Process according to claim 1 in which the fibres are present in the fermenter in an amount from 1 to 20 grams per liter.

3. Process according to claim 2 in which the fibres are present in an amount from 2 to 8 grams per liter.

4. Process according to claim 1 in which the cultivation is carried out with agitation, following which the fibres are decanted and the supernatant recovered.

5. Process according to claim 4 in which after a first cultivation, the supernatant is eliminated, fresh nutritive medium is added and a fresh cultivation carried out, the resulting supernatant being recovered.

6. Process according to claim 1 in which the cells are NIL 2, IFFA 2, WI 38, PK 15 or PRC 5 cells.

7. Process according to claim 1 in which the concentration of cells is from 50,000 to 500,000 cells per milliliter.

8. Process according to claim 1 in which the virus is a strain of rabies virus.

9. Process according to claim 8 in which the strain of rabies virus is a Pasteur, CVS or Pitman Moore fixed type virus or a Flury HEP, Flury LEP, SAD modified virus.

10. Process according to claim 1 in which before inseminating the fermenter, the virus is subjected to adaptation on cells of the chosen type on a suspension of collagen fibres.

11. Process according to claim 10 in which before inseminating the fermenter, the virus is subjected to adaptation on a stationary layer of cells of the selected type.

12. The process of claim 6, wherein said collagen fibers are purified, dehydrated and sterilized prior to use in the step of cultivating and are present in the fermenter in an amount of from 1 to 20 grams per liter.

13. The process of claim 4, wherein said collagen fibers are purified, dehydrated and sterilized prior to use in said step of cultivating and are present in the fermenter in an amount of from 1 to 20 grams per liter.

14. The process of claim 12, in which the cultivation is carried out with agitation following which the fibers are decanted and the supernatant recovered.

* * * * *

UNITED STATES PATENT AND TRADEMARK OFFICE
CERTIFICATE OF CORRECTION

PATENT NO. : 4,169,761

DATED : October 2, 1979

INVENTOR(S) : Pierre Precausta, Marc Bugand, Philippe Comte, and Georges Zwingelstein It is certified that error appears in the above-identified patent and that said Letters Patent are hereby corrected as shown below:

On the title page, first inventor's address should be corrected as follows:

Delete "1700 Big Trail Road, Walled Lake, Mich. 48088" and insert --Thurins--.

Claim 6, line 2, "IFFA2" should read --IFFA3--.
"PRC5" should read --MRC5--.

Signed and Sealed this

Twenty-second Day of April 1980

[SEAL]

Attest:

SIDNEY A. DIAMOND

Attesting Officer

Commissioner of Patents and Trademarks